United States Patent [19]

Schubert et al.

[11] Patent Number: 5,117,119
[45] Date of Patent: May 26, 1992

[54] AUTO-RANGING FILM DENSITOMETER

[75] Inventors: Paul C. Schubert, Marine; Richard R. Lemberger, Forest Lake, both of Minn.

[73] Assignee: Minnesota Mining and Manufacturing Company, St. Paul, Minn.

[21] Appl. No.: 668,490

[22] Filed: Mar. 13, 1991

[51] Int. Cl.$^5$ ............................................. G01N 21/22
[52] U.S. Cl. ........................... 250/559; 250/214 AG; 356/443; 356/444
[58] Field of Search .......... 250/559, 214 AG, 214 A; 356/443, 444, 224

[56] References Cited

U.S. PATENT DOCUMENTS

| | | | |
|---|---|---|---|
| 3,902,813 | 9/1975 | Vanden Broek et al. | 356/444 |
| 3,918,815 | 11/1975 | Gadbois | 250/559 |
| 3,942,898 | 3/1976 | Anderson | 250/559 |
| 4,150,899 | 4/1979 | Nakamura | 356/444 |
| 4,424,589 | 3/1984 | Thomas et al. | 382/61 |
| 4,557,604 | 12/1985 | Gephart | 356/443 |
| 4,603,956 | 8/1986 | Baker | 356/443 |
| 4,697,236 | 9/1987 | Butts et al. | 356/39 |
| 4,700,058 | 10/1987 | Belanger et al. | 250/205 |
| 4,757,334 | 7/1988 | Volent | 364/76 |

Primary Examiner—Janice A. Howell
Assistant Examiner—Kiet T. Nguyen
Attorney, Agent, or Firm—Gary L. Griswold; Walter N. Kirn; Walter C. Linder

[57] ABSTRACT

A film densitometer for generating digital density values as a function of analog transmittance signals received at an input. A comparator coupled to the input compares the transmittance signals to one or more range references characterizing a plurality of ranges of transmittance signal magnitudes, and provides digital transmittance range signals as a function of the comparison. An amplifier amplifies the transmittance signals to provide amplified transmittance base signals. A gain control circuit coupled to the amplifier and the comparator controls the gain factor of the amplifier as a function of the magnitudes of the transmittance signals. The amplified transmittance base signals are converted to digital transmittance base values by an analog-to-digital converter. A lookup table of data characterizing the logarithmic relationship between transmittance base values and density base values is stored in base memory. A lookup table of data characterizing the relationship between the transmittance range signals and range gain values is stored in range memory. A digital processor accesses the memory as a function of the transmittance base values and transmittance range signals, and generates the digital density values as a function of a sum of the density base values and range gain values.

13 Claims, 3 Drawing Sheets

| RANGE SIGNALS FROM CIRCUIT 60 $R_A$ $R_B$ | TRANSMITTANCE VALUES | DENSITY VALUES | GAIN FACTOR OF AMPLIFIER 58 | RANGE GAIN VALUES RGV |
|---|---|---|---|---|
| 1  1 | $1.000 > T \geq 0.100$ | $0.00 < D \leq 1.00$ | 1 | 0 |
| 0  1 | $0.100 > T \geq 0.010$ | $1.00 < D \leq 2.00$ | 10 | 100 |
| 0  0 | $0.010 > T$ | $2.00 < D$ | 100 | 200 |

Fig 4

AUTO-RANGING FILM DENSITOMETER

BACKGROUND OF THE INVENTION

The present invention relates generally to photographic film processing systems. In particular, the present invention is a densitometer for providing information representative of the density (degree of lightness or darkness) of images on the film.

Electronic imaging systems are widely used in the medical field. Imaging systems of this type include a Computed Tomography (CT), Magnetic Resonance (MR) or other type of scanner to generate the image data, and an imager responsive to the data for exposing the image on photographic film. The film is subsequently developed in a film processor to produce a hard copy of the image.

The image on the developed film is formed from areas which vary in lightness and darkness. In order for medical personnel to make accurate diagnoses, the areas of lightness and darkness must accurately represent the image data generated by the scanner. To this end, densitometers are typically used for determining the density, or degree of lightness or darkness, of various portions of the film. Information representative of measured film density is then used by the imager and/or film processor to optimize the density of subsequently imaged and developed film.

The density (D) of an exposed and developed area of film is defined as the common logarithm of the inverse of the transmittance (T) (i.e., $D = \log_{10}(T^{-1})$). The transmittance is defined as the portion of incident light impinging upon one side of the film which passes through the film. Known densitometers typically include a light emitting subsystem with a light source for impinging light on a selected area of the film. A light detecting subsystem including a photosensitive element such as a photodiode is positioned on the other side of the film, and detects the portion of light passing through the film. Circuitry coupled to the light detecting subsystem determines the transmittance, and generates signals representative of the film density in accordance with the equation given above. The densitometer circuitry typically includes a logarithmic amplifier since a large range of signals must be detected and amplified. By way of example, the light intensity reaching the photodetector is down by a factor of 2000 for a density of 3.3 from the light intensity corresponding to a density of 0.0. Unfortunately, logarithmic amplifiers are relatively costly and are not available in monolithic form.

Other densitometers are discussed and disclosed in the Thomas et al. U.S. Pat. No. 4,424,589. In the Field And Background Of The Invention section it is noted that prior systems used either an analog method of logging, or a digital method using an analog-to-digital converter and a memory lookup table containing the logarithmic values. The scanner system disclosed in the patent includes three sets of analog-to-digital converters associated and memory devices to convert a range of analog signals into corresponding digital density values. The range of analog signals is divided into three amplitude bands. Each set of converters and memory devices operates on signals within one of the bands to reduce the wasted resolution capacities of the converters and memories at high intensity levels.

The Bellanger et al. U.S. Pat. No. 4,700,058 discloses an imaging system which incorporates feedback control techniques to provide control of film density. A first feedback loop monitors light intensity from the film writing device and provides a feedback signal to a variable gain amplifier to maintain the light output of the writing device at a desired level. A second feedback control loop monitors the density of the exposed and developed film, and provides feedback signals to a variable gain amplifier. By changing the gain of the amplifier, the image data signal is adjusted in such a manner as to correct for any deviations from a desired film density. The system also includes a digital memory for storing a lookup table of film reference density settings as a function of voltage levels.

The Volent U.S. Pat. No. 4,757,334 discloses a film imaging and processing system with a density correction system. Film used with the system includes a density calibration strip. Densities of the calibration strip are monitored by a densitometer after the film has been developed. The film densities of the developed calibration strip are then compared to a predetermined standard to determine any variations. In response, a correction signal is applied to the scanner to adjust the density on subsequently exposed sheets of film.

It is evident that there is a continuing need for improved densitometers for photographic film imaging and processing systems. The densitometers must quickly and accurately generate signals representative of film density. To be commercially viable, the densitometers must also be capable of implementation with relatively inexpensive electronic components.

SUMMARY OF THE INVENTION

The present invention is a highly accurate yet inexpensive film densitometer which provides digital density values as a function of a large range of transmittance signals received at an input. The densitometer includes a range detector circuit which is coupled to the input and provides digital transmittance range signals characterizing the magnitudes of the transmittance signals as being within one of a plurality of ranges. An analog amplifier is coupled to the input and provides amplified transmittance base signals. The gain of the amplifier is controlled by a gain control circuit as a function of the magnitudes of the transmittance signals. The amplified transmittance base signals generated by the amplifier are converted to digital transmittance base values by an analog-to-digital converter. Digital processing circuitry coupled to the converter and range detector circuit generates the digital density values as a logarithmic function of the transmittance base values and the transmittance range signals.

In one embodiment the range detector circuit includes comparator circuitry for comparing the transmittance signals to range references representative of a negative one factor of ten range, a negative two factor of ten range and a negative three factor of ten range of transmittance signal magnitudes. The gain control circuit includes circuitry for causing the analog amplifier to have a gain of unity when the magnitude of the transmittance signals is within the negative one factor of ten range, a gain of ten when the magnitude of the transmittance signals is within the negative two factor of ten range, and a gain of one hundred when the magnitude of the transmittance signals is within the negative three factor of ten range.

In other embodiments the digital processing circuitry includes base memory, range memory and a processor. Data characterizing the logarithmic relationship between transmittance base values and corresponding density base values is stored in the base memory. Data characterizing the relationship between transmittance range signals and range gain values is stored in the range memory. The processor accesses the base memory and range memory as a function of the transmittance base values and range signals to determine associated density base values and density range values, and generates the digital density values as a function of a sum of the accessed density base values and density range values.

BRIEF DESCRIPTION OF THE DRAWINGS

FIG. 4 is an illustration of a table of information referenced in the Detailed Description of The Preferred Embodiments section.

DETAILED DESCRIPTION OF THE PREFERRED EMBODIMENTS

Figure 1:
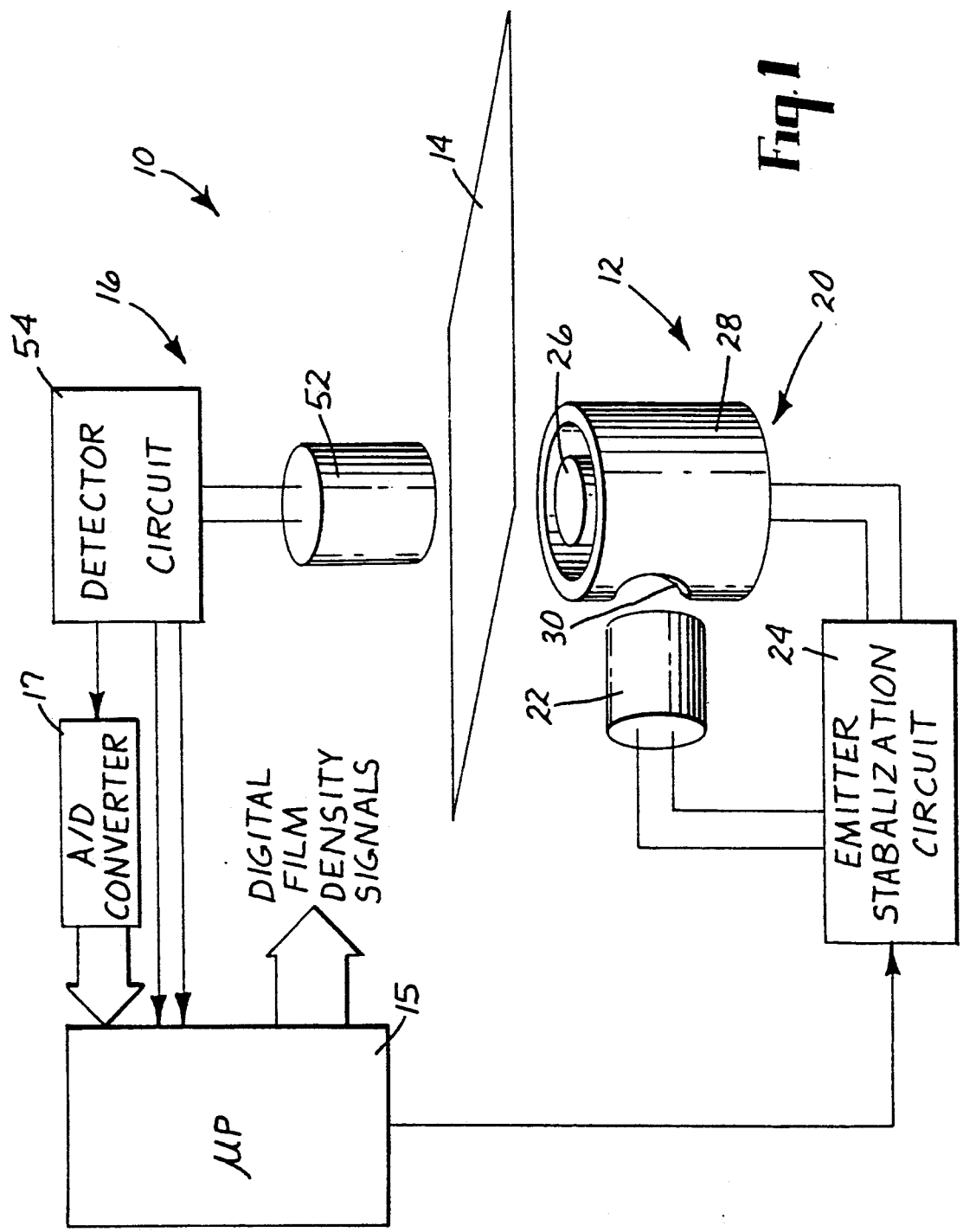
FIG. 1 is a block diagram representation of a film densitometer in accordance with the present invention.

An auto-ranging film densitometer 10 in accordance with the present invention is illustrated generally in FIG. 1. As shown, densitometer 10 includes a radiation or light emitting subsystem 12, light detecting subsystem 16 and microprocessor 15. Light emitting subsystem 12 generates and impinges light of a known magnitude or intensity upon a predetermined portion of film 14. Light detecting subsystem 16 senses the portion of the impinged light which passes through film 14, and generates amplified transmittance base signals and transmittance range signals which together characterize the transmittance (T) of the film (the fraction of impinged light which passes through). Film density (D) is defined as the common logarithm of the inverse of the transmittance (ie, $D = \log_{10}(T^{-1})$), and is an indication of the degree of lightness or darkness of the image on film 14. Microprocessor 15 generates digital density value signals representative of the film density as a function of the transmittance base and transmittance range signals.

As shown in FIG. 1, light emitting subsystem 12 includes a light emitting diode (LED) assembly 20, photodiode 22 and emitter stabilization circuit 24. LED assembly 20 includes a red LED 26 mounted within a barrel 28. Photodiode 22, which is a p.i.n. photodiode in one embodiment, is positioned adjacent to an aperture 30 through the side of barrel 28 to monitor the intensity of light emitted by LED assembly 20.

Emitter stabilization circuit 24 utilizes signals received from photodiode 22 in a closed feedback loop to initiate a constant and stable light intensity output from LED 26. Stabilized light intensity control is thereby achieved without having to position any optical components in the light path between LED 26 and film 14. Light emitting subsystem 12 and its LED 26 can be turned On and Off by microprocessor 15 in response to signals received by emitter stabilization circuit 24.

Figure 2:
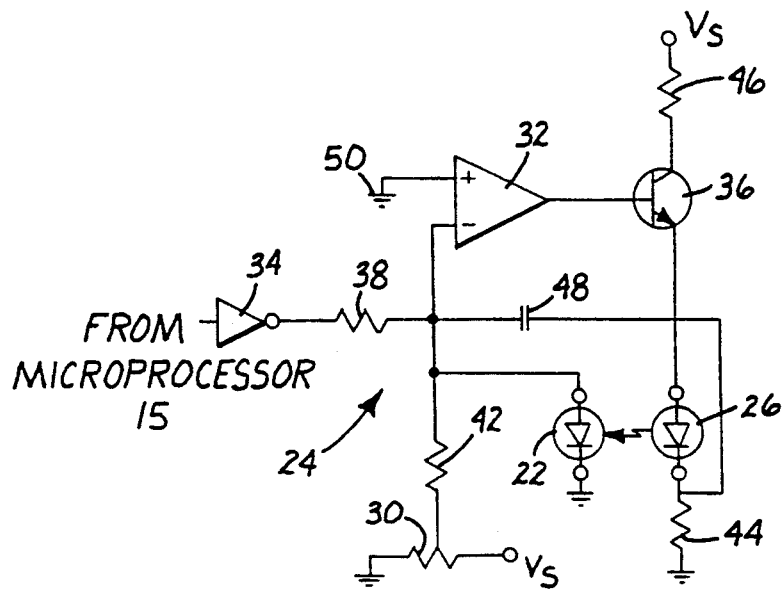
FIG. 2 is a detailed circuit diagram of the light emitter stabilization circuit shown in FIG. 1.

Emitter stabilization circuit 24 and its electrical interconnections to microprocessor 15, photodiode 22 and LED 26 are illustrated in greater detail in FIG. 2. As shown, emitter stabilization circuit 24 includes potentiometer 30, operational amplifier 32, inverter 34, transistor 36, resistors 38, 42, 44, and 46, and capacitor 48. These circuit elements are electrically interconnected between ground terminal 50 and a positive supply potential $V_s$. Feedback capacitor 48 provides AC stabilization. A logic LO signal received at the input of inverter 34 from microprocessor 15 disables light emitting subsystem 20. A logic HI signal at the input of inverter 34 enables drive current flow to and light emission from LED 26. The magnitude of the drive current supplied to LED 26, and therefore the intensity of the light beam produced by the LED, is controlled by transistor 36 in response to a bias signal applied to the base of the transistor by amplifier 32. Amplifier 32 has an inverting (−) input terminal connected to receive feedback signals from the anode of photodiode 22 and the cathode of LED 26, and thereby regulates the intensity of the light beam produced by the LED. The quiescent output level of LED 26 is controlled by potentiometer 30.

Referring back to FIG. 1, light detecting subsystem 16 is shown to include a p.i.n. photodiode 52 and a detector circuit 54. Photodiode 52 is positioned to receive light transmitted through film 14. In response, photodiode 52 generates currents (ie., transmittance signals) representative of the amounts of light received. Transmittance base signals representative of the magnitudes of the photodiode currents, and transmittance range signals characterizing the magnitudes of the photodiode currents as being within one of several ranges, are generated by detector circuit 54 as a function of the photodiode currents. The transmittance base signals generated by detector circuit 54 are digitized by analog-to-digital (A/D) converter 17 before being applied to microprocessor 15. In the embodiment illustrated in FIG. 1, detector circuit 54 generates digital transmittance range signals which are applied directly to microprocessor 15.

Figure 3:
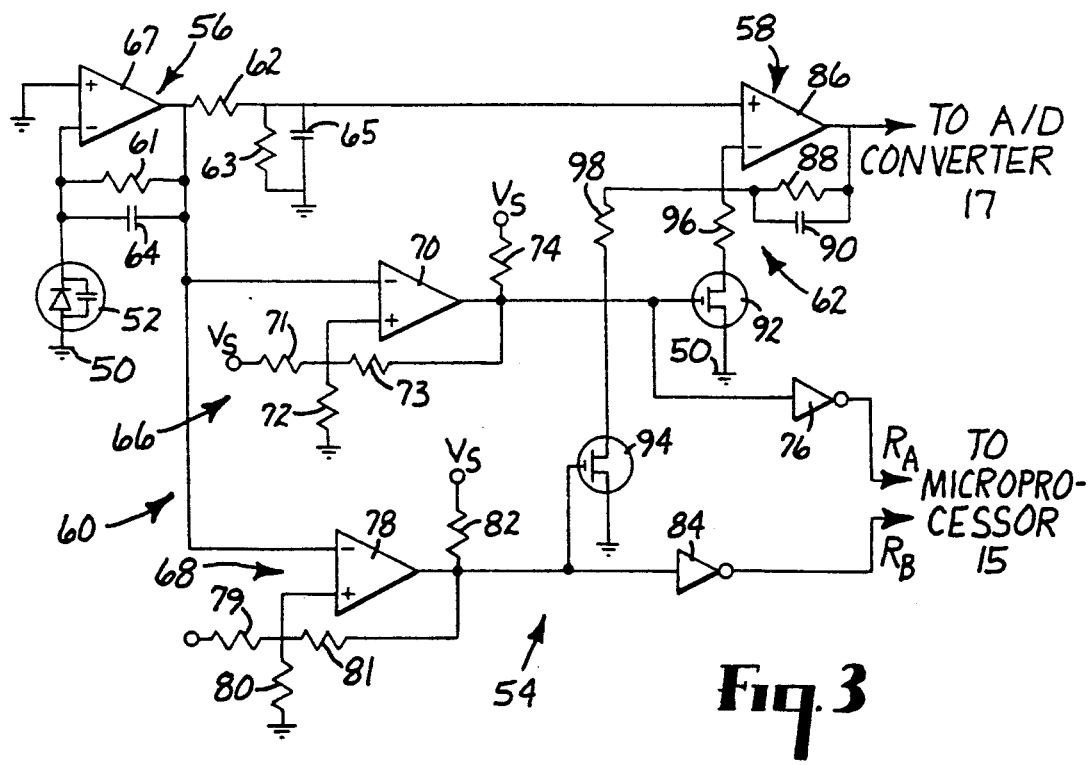
FIG. 3 is a detailed circuit diagram of the detector circuit shown in FIG. 1.

Detector circuit 54 and its interconnections to photodiode 52, A/D converter 17 and microprocessor 15 are illustrated in greater detail in FIG. 3. As shown, detector circuit 54 includes a transimpedance (current-to-voltage) amplifier 56, amplifier 58, range detector circuit 60 and gain control circuit 62. Transimpedance amplifier 56 is connected to receive the current signal from photodiode 52 and includes operational amplifier 67, resistors 61, 62, and 63, and capacitors 64 and 65. The inverting (−) input terminal of amplifier 67 is connected to ground terminal 50 through photodiode 52, while the noninverting (+) input terminal is connected directly to the ground terminal. Resistor 61 and capacitor 64 are connected in a parallel circuit between the output and inverting input terminals of amplifier 67. The output terminal of amplifier 67 is connected to ground terminal 50 through the series arrangement of resistor 62 and the parallel combination of resistor 63 and capacitor 65. Transimpedance amplifier 56 converts the current signals produced by photodiode 52 to voltage signals of proportional magnitudes.

In the embodiment shown in FIG. 3, range detector circuit 60 includes first range comparator circuit 66 and second range comparator circuit 68. Comparator circuits 66 and 68 compare the voltage transmittance signals to reference voltages representative of several adjacent factor of ten ranges of transmittance signal magnitudes, and provide range signals $R_A$ and $R_B$ indicating the ranges within which the transmittance signals lie. Range comparator circuit 66 includes voltage comparator (VC) 70, resistors 71–74 and inverter 76. The inverting (−) input terminal of VC 70 is connected to the output of operational amplifier 67. Resistors 71 and 72 are connected in series between supply potential $V_s$ and ground terminal 50. Resistor 73 is interconnected between the noninverting (+) input terminal and output terminal of VC 70 to provide hysteresis. The output terminal of VC 70 is also coupled to supply potential $V_s$ through resistor 74 and to microprocessor 15 through inverter 76. Resistors 71 and 72 function as a voltage divider and are ratioed to provide a range reference voltage at the noninverting input terminal of VC 70 having a magnitude corresponding to a transmittance signal magnitude representative of a transmittance of 0.100 (i.e., a −1 factor of 10 transmittance which corresponds to a density of 1.00). The transmittance range signals $R_A$ produced at the output of inverter 76 will therefore be at logic LO levels for transmittance signal magnitudes representative of transmittance values less than 0.100, and at logic HI levels for transmittance signal magnitudes representative of transmittance values greater than or equal to 0.100.

Range comparator 68 is configured in a manner similar to that of comparator 60 described above, and includes VC 78, resistors 79–82 and inverter 84. Resistors 79 and 80 function as a voltage divider and are ratioed to provide a range reference voltage on the noninverting input terminal of VC 78 which corresponds in magnitude to the magnitude of transmittance signals representative of a transmittance value of 0.010 (ie. a −2 factor of 10 transmittance which corresponds to a density of 2.00). Range comparator 68 therefore generates a logic LO transmittance range signal $R_B$ at the output of inverter 84 whenever the magnitude of the transmittance signals received at the inverting input terminal of VC 78 correspond to transmittance values less than 0.010. For transmittance signals having magnitudes corresponding to transmittance values greater than or equal to 0.010, range comparator 68 produces a logic HI transmittance range signal $R_B$.

In the embodiment described above, the outputs of range comparators 66 and 68 are digital signals $R_A$ and $R_B$ representative of transmittance values within three factor of ten ranges (ie. $1.000 > T \geq 0.100$; $0.100 > T \geq 0.010$; and $T < 0.010$). These digital range signals are applied to microprocessor 15 as a two bit signal. The transmittance range signals $R_A$ and $R_B$ and corresponding transmittance values and density ranges are illustrated in FIG. 4.

The amplification gain factor of amplifier 58 is controlled by gain control circuit 62 as a function of the transmittance range signals produced by range detector circuit 60. Amplifier 58 includes operational amplifier 86, resistor 88 and capacitor 90. The noninverting (+) input terminal of amplifier 86 is connected to receive the transmittance signals from the output of transconductance amplifier 56. Resistor 88 and capacitor 90 are connected in a parallel circuit between the output and the inverting (−) input terminals of amplifier 86. Amplifier 58, range detector circuit 60 and gain control circuit 62 function as a nonlinear amplifier of the transmittance signals received from transconductance amplifier 56, amplifying these signals as a function of their magnitudes to produce amplified transmittance base signals at the output of operational amplifier 86.

Gain control circuit 62 includes FETs 92 and 94 and resistors 96 and 98. The gate of FET 92 is coupled to the output terminal of VC 70 of range comparator 66. Resistor 96 is interconnected between the inverting input terminal of operational amplifier 86 and the drain of FET 92. The source of FET 92 is coupled to ground terminal 50. In a similar manner the gate of FET 94 is connected to the output terminal of VC 78 of range comparator 68, while resistor 98 and the source-drain channel of the FET are connected in a series circuit between the inverting input terminal of amplifier 86 and ground terminal 50.

FETs 92 and 94 function as switches causing resistors 96 and 98, respectively, to be electrically interconnected to amplifier 58 as a function of the output of respective range comparators 66 and 68. The DC gain factor of amplifier 58 is determined as a function of the resistance value of resistor 88 and the value of whichever resistors 96 and 98 are electrically coupled to amplifier 86. The outputs of VCs 70 and 78 will be at logic LO levels whenever the transmittance signals have magnitudes greater than the associated reference voltages of range comparators 66 and 68. When the outputs of VCs 70 and 78 are at logic LO levels, FETs 94 and 96 will be OFF, electrically disconnecting resistors 96 and 98, respectively, from amplifier circuit 58. Amplifier 58 will therefore have a first DC gain factor for transmittance signals representative of transmittance values within the first range detected by range detector circuit 60.

In response to transmittance signals having magnitudes representative of transmittance values within the second range detected by circuit 60, the output of VC 70 will be at a logic HI while the output of VC 78 will be at a logic LO. FET 92 is switched ON in response to the logic HI signal applied to its gate, electrically interconnecting resistor 96 to operational amplifier 86. Amplifier 58 will therefore have a second DC gain factor determined by the resistance values of resistors 88 and 96. In a similar manner, when the magnitudes of the transmittance signals are representative of transmittance values within the third range for which range detector circuit 60 is configured to detect, the outputs of VCs 70 and 78 will both be at a logic HI level. Both FETs 92 and 94 will therefore be switched ON, electrically interconnecting their associated resistors 96 and 98 to operational amplifier 86. Amplifier 58 will therefore have a third DC gain factor determined as a function of the values of resistors 88, 96, and 98.

In the embodiment of detector circuit 54 described above, range detector circuit 60 is configured to determine whether the transmittance signals have magnitudes corresponding to transmittance values within either a first factor of ten range from 1.000 to 0.100, a second factor of ten range from 0.100 to 0.010 or a third factor of ten range less than 0.010. In this embodiment resistors 88, 98, and 96 can have resistance values which cause amplifier 58 to have a gain factor of one for transmittance values within the first factor of ten range, a gain factor of ten for transmittance values within the second factor of ten range, and a gain factor of one hundred for transmittance values within the third range. These gain factors and the corresponding range signals, transmittance values and density values are illustrated in FIG. 4.

Referring back to FIG. 1, microprocessor 15 is connected to receive the amplified transmittance base signals and transmittance range signals from detector circuit 54. The transmittance range signals $R_A$ and $R_B$ generated by detector circuit 54 in the example described above are in digital form and are applied directly to microprocessor 15. The amplified transmittance base signals are converted to digital transmittance base values (TBV) by A/D converter 17 before being applied to microprocessor 15. In one embodiment A/D converter 17 is a 10-bit converter.

Emitter stabilization circuit 24 and detector circuit 54 are also configured in such a manner that the magnitude of the amplified transmittance base signals produced by amplifier 58 for the maximum transmittance signal (ie., that representative of a transmittance of 1.0 and a density of 0.0) is 80% of the level required for the maximum output count for A/D converter 17. In this configuration A/D converter 17 will produce a transmittance base value TBV of 818 (80% of $2^{10}$) for transmittance signal magnitudes corresponding to a transmittance of 1.000. This arrangement prevents A/D converter 17 from being saturated or receiving input signals which exceed its maximum input voltage.

Microprocessor 15 includes associated memory (RAM or ROM, not shown), and is programmed to generate 16-bit digital density value signals representative of the density of the image on film 14 as a function of the received 10-bit transmittance base values TBV and the transmittance range signals $R_A$ and $R_B$. To facilitate the digital density calculations from these input signals, microprocessor 15 includes a base memory portion programmed with information characterizing 16-bit density base values (DBV) as a common logarithmic function of associated 10-bit transmittance base values TBV. In one embodiment, microprocessor 15 includes base memory programmed with a lookup table of transmittance base values TBV and associated density base values DBV. The lookup table in the base memory portion is accessed as a function of the transmittance base values TBV to determine the associated density base values DBV. The functional relationship between transmittance base values TBV and density base values DBV is given by Equations 1 and 2 below:

$$DBV = Int\ [100(\log_{10}(818/TBV))] \qquad EQ.\ 1$$

for $1 < TBV < 818$ $$DBV = 291 \qquad EQ.\ 2$$

for $TBV = 0$

The division of the transmittance base values TBV into 818 is done to scale the calculation to the expected full scale 0–818 range of base values received from 10-bit A/D converter 17. The multiplication factor of 100 is used to facilitate calculations in whole numbers, and as described below, is factored out during the final calculation of the digital film density values. The function "Int" rounds the calculation of density base values DBV to the nearest integer. As shown by Equation 2, the density base value DBV associated with transmittance base values TBV of 0 is 291. This special case occurs only for film 14 having an extremely high density image, or when no light is being generated by light emitting subsystem 12.

An ideal digital film density value $D_{ideal}$, the density value which would be generated by densitometer 10 if light emitting subsystem 12 was absolutely stable, is calculated by microprocessor 15 as a function of the density base value DBV and a range gain value RGV in accordance with EQ. 3 below.

$$D_{ideal} = (DBV + RGV)/100 \qquad EQ.\ 3$$

The range gain value RGV is a value determined as a function of range signals $R_A$ and $R_B$. For the embodiment of detector circuit 54 described above, FIG. 4 describes the appropriate range gain values RGV as a function of the range signals $R_A$ and $R_B$ received from range detector circuit 60. Range gain values RGV are equal to one hundred times the common logarithm of the amplifier gain factor for the associated range signals. The multiplication factor of 100 scales the range gain values RGV to the density base values DBV calculated in accordance with Equations 1 and 2. This multiplication factor is divided out in accordance with EQ. 3.

Microprocessor 15 also includes a range memory portion (not separately shown) programmed with information characterizing range gain values RGV as a function of range signals $R_A$ and $R_B$. In a preferred embodiment, this information is programmed in a lookup table. The lookup table in the range memory portion is accessed as a function of signals $R_A$ and $R_B$ to determine the associated range gain values RGV.

In practice, the intensity of the beam of radiation generated by light emitting subsystem 12 will vary somewhat over time. An actual or final density value $D_{final}$ which takes into account any possible variations in the intensity of light emitted by subsystem 12 is calculated by microprocessor 15 as a function of the ideal density value $D_{ideal}$ and a calibration density value $D_{cal}$ in accordance with Equation 4.

$$D_{final} = D_{ideal} - D_{cal} \qquad EQ.\ 4$$

Calibration density value $D_{cal}$ is set equal to the value of $D_{ideal}$ generated in a calibration routine during which no film 14 is positioned between light emitting subsystem 12 and light detecting subsystem 16. This calibration routine can be performed periodically, such as when densitometer system 10 is powered up, or prior to the receipt of each new piece of film 14. The use of the calibration density value $D_{cal}$ in conjunction with the ideal density value $D_{ideal}$ in accordance with Equation 4 will result in final density values $D_{final}$ of greater accuracy.

Densitometer 10 offers a number of advantages. This system eliminates the need for a relatively costly logarithmic amplifier, yet accommodates the large range of transmittance signals by providing the most gain for those signals representative of the highest film densities. By breaking up the transmittance signals into a number of ranges, density measurements can be made to an accuracy of 0.01 density units using a relatively inexpensive 10-bit A/D converter.

Although the present invention has been described with reference to preferred embodiments, those skilled in the art will recognize that changes may be made in form and detail without departing from the spirit and scope of the invention.

What is claimed is:

1. A film densitometer, including:
   an input for receiving analog transmittance signals;
   an analog amplifier coupled to the input for amplifying the transmittance signals and providing amplified transmittance base signals;
   a range detector circuit coupled to the input for providing digital transmittance range signals characterizing the magnitudes of the analog transmittance signals as being within one of a plurality of ranges;
   a gain control circuit coupled to the amplifier and range detector circuit for controlling the gain of the amplifier as a function of the magnitudes of the transmittance signals;

an analog-to-digital converter coupled to the amplifier for converting the amplified transmittance base signals to digital transmittance base values; and digital processing circuitry coupled to the converter and the range detector circuit for generating digital density value signals as a logarithmic function of the transmittance base values and the transmittance range signals.

2. The densitometer of claim 1 wherein:

the range detector circuit includes a comparator circuit for comparing the transmittance signals to one or more range references representative of a plurality of ranges of transmittance signal magnitudes, and for providing the transmittance range signals as a function of the comparison; and the gain control circuit is coupled to the comparator circuit and includes circuitry for causing the amplifier to have one of a plurality of gain factors as a function of the transmittance range signals.

3. The densitometer of claim 2 wherein: the comparator circuit includes circuitry for comparing the transmittance signals to one or more range references representative of transmittance signals within a plurality of factor of ten ranges of magnitudes, and for providing the transmittance range signals as a function of the comparison; and the gain control circuit includes circuitry for causing the amplifier to have one of a plurality of factor of ten gain factors.

4. The densitometer of claim 3 wherein: the comparator circuitry includes circuitry for comparing the transmittance signals to range references representative of a negative one factor of ten range, a negative two factor of ten range, and a negative three factor of ten range of transmittance signal magnitudes, and for providing transmittance range signals representative of the factor of ten range as a function of the comparison; and the gain control circuit includes circuitry for causing the amplifier to have a first factor of ten gain when the magnitudes of the transmittance signals are within the negative one factor of ten range, a second factor of ten gain when the magnitudes of the transmittance signals are within a negative two factor of ten range, and a third factor of ten gain when the magnitudes of the transmittance signals are within the negative three factor of ten range.

5. The densitometer of claim 4 wherein the gain control circuit includes circuitry for causing the first factor of ten gain to be a gain factor of unity, the second factor of ten gain to be a gain factor of ten, and the third factor of ten gain to be a gain factor of one hundred.

6. The densitometer of claim 4 wherein the comparator circuit includes circuitry for providing a 2-bit digital transmittance range signal.

7. The densitometer of claim I wherein the digital processing circuitry includes:

base memory for storing data characterizing the logarithmic relationship between transmittance base values and density base values;

range memory for storing data characterizing the relationship between transmittance range signals and density range gain values; and a processor for accessing the base memory and range memory as a function of the transmittance base values and transmittance range signals to determine associated density base values and density range values, and for generating digital density values as a function of a sum of the density base values and density range values.

8. The densitometer of claim 7 wherein:

the base memory includes a lookup table for storing an array of transmittance base values and corresponding density base values; and the range memory includes a lookup table for storing an array of transmittance range signals and associated range gain values.

9. A film densitometer including:

an input for receiving analog transmittance signals;

a comparator coupled to the input for comparing the transmittance signals to one or more range references characterizing a plurality of ranges of transmittance signal magnitudes, and for providing digital transmittance range values as a function of the comparison;

an analog amplifier coupled to the input for amplifying the transmittance signals and providing amplified transmittance base signals;

an amplifier gain control circuit coupled to the amplifier and comparator, for controlling the gain factor of the amplifier as a function of the magnitudes of the transmittance signals;

an analog-to-digital converter coupled to the amplifier for converting the amplified transmittance base signals to digital transmittance base values;

base memory for storing data characterizing a logarithmic relationship between transmittance base values and density base values;

range memory for storing data characterizing a relationship between transmittance range values and density range gain values; and a processor coupled to the comparator, amplifier, base memory and range memory, for accessing the base memory and range memory as a function of the transmittance base values and transmittance range values, and for generating digital density values as a function of a sum of the density base values and the density range gain values.

10. The densitometer of claim 9 wherein:

The comparator includes circuitry for comparing the transmittance signals to one or more range references representative of transmittance signals having magnitudes within a plurality of factor of ten ranges of magnitudes, and for providing the transmittance range values as a function of the comparison; and the gain control circuit includes circuitry for causing the amplifier to have one of a plurality of factor of ten gain factors.

11. The densitometer of claim 9 wherein:

The comparator includes circuitry for comparing the transmittance signals to range references representative of a negative one factor of ten range, a negative two factor of ten range, and a negative three factor of ten range cf transmittance signal magnitudes, and for providing the transmittance range values as a function of the comparison; and the gain control circuit includes circuitry for causing the amplifier to have a first factor of ten gain when the magnitudes of the transmittance signals are within the negative one factor of ten range, a second factor of ten gain when the magnitudes of the transmittance signals are within the negative two factor of ten range, and a third factor of ten gain when the magnitudes of the transmittance signals are within the negative three factor of ten range.

12. The densitometer of claim 11 wherein the gain control circuit includes circuitry for causing the first factor of ten gain to be a gain factor of unity, the second factor of ten gain to be a gain factor of ten, and the third factor often gain to be a gain factor of one hundred.

13. The densitometer of claim 9 wherein:
the base memory includes a lookup table for storing an array of transmittance base values and corresponding density base values; and
the range memory includes a lookup table for storing an array of transmittance range signals and associated range gain values.

* * * * *